(12) United States Patent
Inoue (10) Patent No.: US 10,413,321 B2
(45) Date of Patent: Sep. 17, 2019

(54) TROCAR SENSOR UNIT AND TROCAR (71) Applicant: OLYMPUS CORPORATION, Tokyo (JP)

(72) Inventor: Shintaro Inoue, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 128 days.

(21) Appl. No.: 15/396,971

(22) Filed: Jan. 3, 2017

(65) Prior Publication Data
US 2017/0112527 A1 Apr. 27, 2017

Related U.S. Application Data (63) Continuation of application No. PCT/JP2015/069811, filed on Jul. 9, 2015.

(30) Foreign Application Priority Data

Jul. 10, 2014 (JP) .................................. 2014-142495

(51) Int. Cl.
A61B 17/34 (2006.01)
A61B 1/00 (2006.01)
G02B 23/24 (2006.01)

(52) U.S. Cl.
CPC .................. A61B 17/34 (2013.01); A61B 1/00 (2013.01); A61B 17/3494 (2013.01); G02B 23/24 (2013.01)

(58) Field of Classification Search
CPC .......... A61M 39/06; A61M 2039/0626; A61B 17/3421; A61B 17/3423; A61B 17/3462; A61B 2017/3464

(Continued)

(56) References Cited

U.S. PATENT DOCUMENTS 5,713,869 A 2/1998 Morejon
8,025,641 B2 * 9/2011 Bettuchi ............ A61B 17/3462
604/167.01

(Continued)

FOREIGN PATENT DOCUMENTS

CN 1891138 A 1/2007
EP 1 803 388 A2 7/2007

(Continued)

OTHER PUBLICATIONS

Extended Supplementary European Search Report dated Feb. 26, 2018 in European Patent Application No. 15 81 9750.9.

(Continued)

Primary Examiner — Julianna N Harvey
Assistant Examiner — Christina NegrelliRodriguez
(74) Attorney, Agent, or Firm — Scully, Scott, Murphy & Presser, P.C.

(57) ABSTRACT

A trocar sensor unit including a base that is configured to be attached to and detached from a trocar and that has a through-hole through which an insertion section to be inserted into the trocar is inserted; a moving member that has a pressing surface forming at least a portion of an inner surface of the through-hole of the base and that is configured to be moved in a radial direction of the through-hole; and a sensor that is disposed in at least one of the moving member and a portion of the inner surface of the through-hole opposite the pressing surface and that detects the amount of movement of a surface of the insertion section in the through-hole.

18 Claims, 9 Drawing Sheets (58) Field of Classification Search
USPC .................. 600/201, 202, 204; 604/174, 178
See application file for complete search history.

(56) References Cited

U.S. PATENT DOCUMENTS

| | | |
|---|---|---|
| 2007/0149856 A1 | 6/2007 | Segawa |
| 2008/0146875 A1 | 6/2008 | Noguchi et al. |
| 2009/0281478 A1 | 11/2009 | Duke |
| 2014/0171873 A1 | 6/2014 | Mark |

FOREIGN PATENT DOCUMENTS

| | | |
|---|---|---|
| EP | 1 902 662 A1 | 3/2008 |
| EP | 2 116 201 A1 | 11/2009 |
| JP | S56-148331 A | 11/1981 |
| JP | H05-337127 A | 12/1993 |
| JP | H08-238209 A | 9/1996 |
| JP | 2002-360594 A | 12/2002 |
| JP | 2007-175230 A | 7/2007 |
| JP | 2009-273883 A | 11/2009 |
| JP | 4546043 B2 | 9/2010 |

OTHER PUBLICATIONS

International Search Report dated Oct. 6, 2015 issued in PCT/JP2015/069811.
Chinese Office Action dated Jul. 27, 2018 in Chinese Patent Application No. 201580036123.3.

\* cited by examiner

Figure 11:
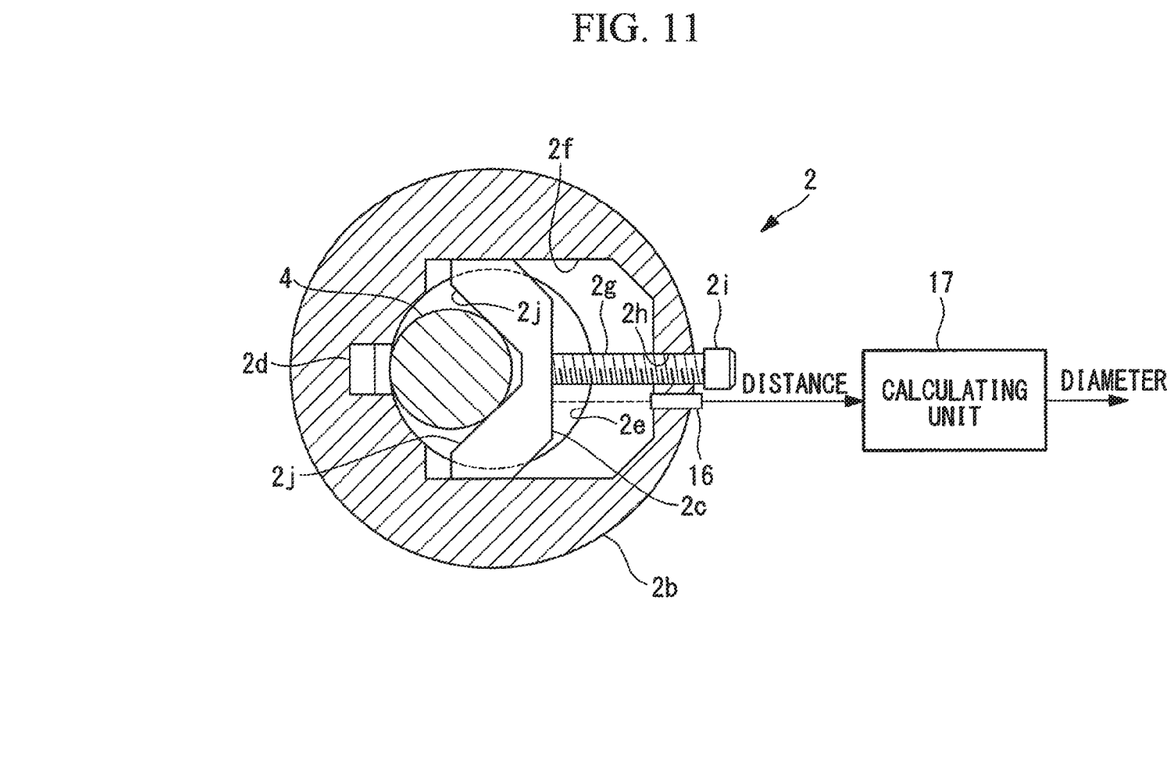
FIG. 11 is a cross-sectional view showing a sixth modification of the trocar sensor unit in FIG. 1.

FIG. 12 ized with the diameter of the insertion section 4, the amount of movement of the moving member 2c in the radial direction of the through-hole 3c can be detected by the sensor 2d, which allows the diameter of the insertion section 4 to be detected.

TROCAR SENSOR UNIT AND TROCAR

CROSS-REFERENCE TO RELATED APPLICATIONS

This is a continuation of International Application PCT/JP2015/069811, with an international filing date of Jul. 9, 2015, which is hereby incorporated by reference herein in its entirety. This application claims the benefit of Japanese Patent Application No. 2014-142495, the content of which is incorporated herein by reference.

TECHNICAL FIELD

The present invention relates to trocar sensor units and trocars.

BACKGROUND ART

There is a known technique in which a trocar, which is used in laparoscopic surgery and is placed in an opening formed in the skin to allow an endoscope or treatment instrument to be inserted into the body, is provided with a depth-of-insertion detecting unit that detects the depth of insertion of an insertion section of the endoscope or treatment instrument (see, for example, Patent Literature PTL 1). This technique uses the depth-of-insertion detecting unit to detect the depth of insertion of the insertion section by measuring the amount of rotation of a roller in contact with the outer surface of the insertion section.

CITATION LIST

Patent Literature

{PTL 1}
Publication of Japanese Patent No. 4546043

SUMMARY OF INVENTION

One aspect of the present invention is a trocar sensor unit including a base that is configured to be attached to and detached from a trocar and that has a through-hole through which an insertion section to be inserted into the trocar is inserted; a moving member that has a pressing surface forming at least a portion of an inner surface of the through-hole of the base and that is configured to be moved in a radial direction of the through-hole; and a sensor that is disposed in at least one of the moving member and a portion of the inner surface of the through-hole opposite the pressing surface and that detects the amount of movement of a surface of the insertion section in the through-hole.

Another aspect of the present invention is a trocar including a base that has a through-hole through which an insertion section is inserted and that is inserted through and fixed in an opening in a skin; a moving member that has a pressing surface forming at least a portion of an inner surface of the through-hole of the base and that is configured to be moved in a radial direction of the through-hole; and a sensor that is disposed in at least one of the moving member and a portion of the inner surface of the through-hole opposite the pressing surface and that detects the amount of movement of a surface of the insertion section in the through-hole.

DESCRIPTION OF EMBODIMENTS

A trocar sensor unit according to an embodiment of the present invention will be described below with reference to the drawings.

Figure 1:
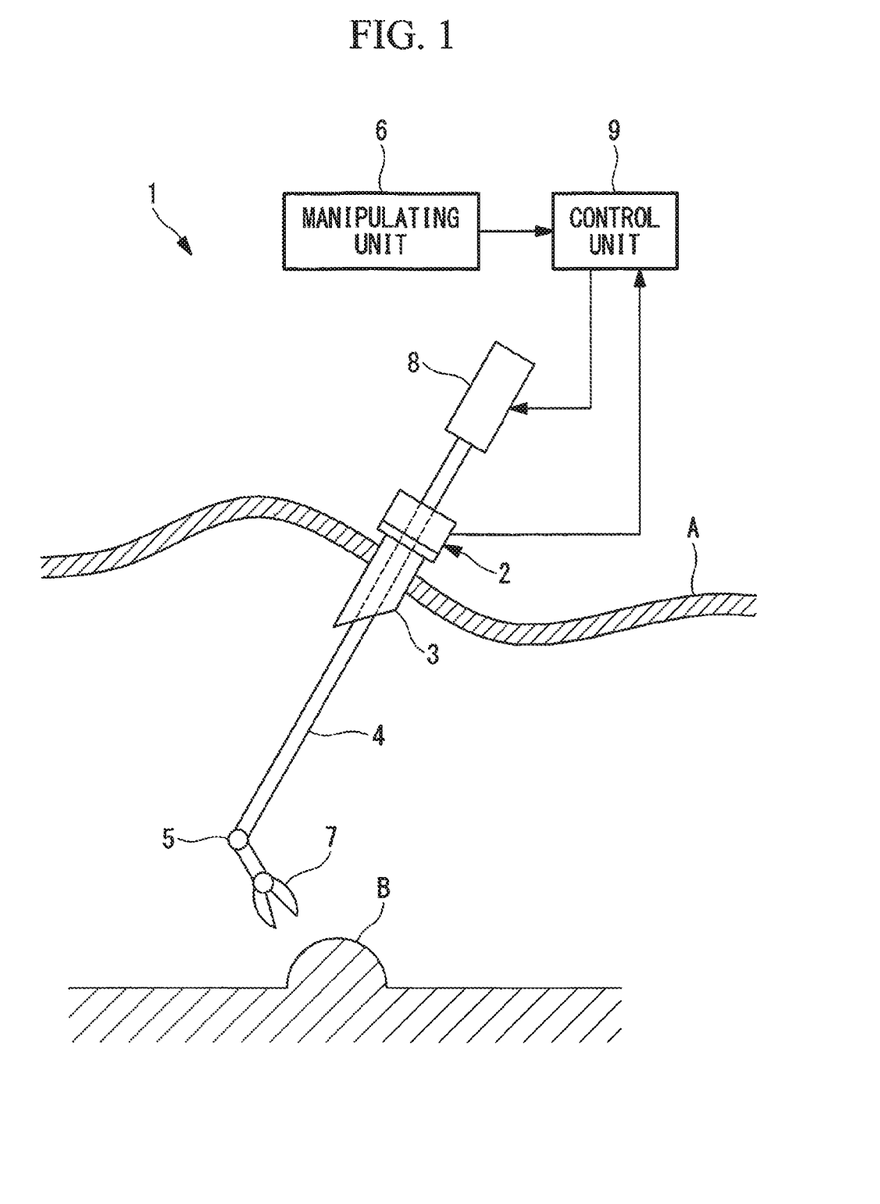
FIG. 1 is an overall view showing a manipulator system including a trocar sensor unit according to an embodiment of the present invention.

As shown in FIG. 1, for example, a trocar sensor unit 2 according to this embodiment is used in a manipulator system 1 for laparoscopic surgery and is configured to be attached to and detached from a trocar 3 placed through skin A.

The manipulator system 1 includes an elongated rigid insertion section 4 for insertion through the trocar 3, a manipulating unit 6 for manually designating the pivot angle of a joint 5 disposed at the distal end of the insertion section 4, an actuating unit 8 for actuating the joint 5, and a control unit 9 for controlling the actuating unit 8. For example, a treatment instrument 7 for treatment of an affected area B in the body is disposed at the distal end of the joint 5.

Figure 2:
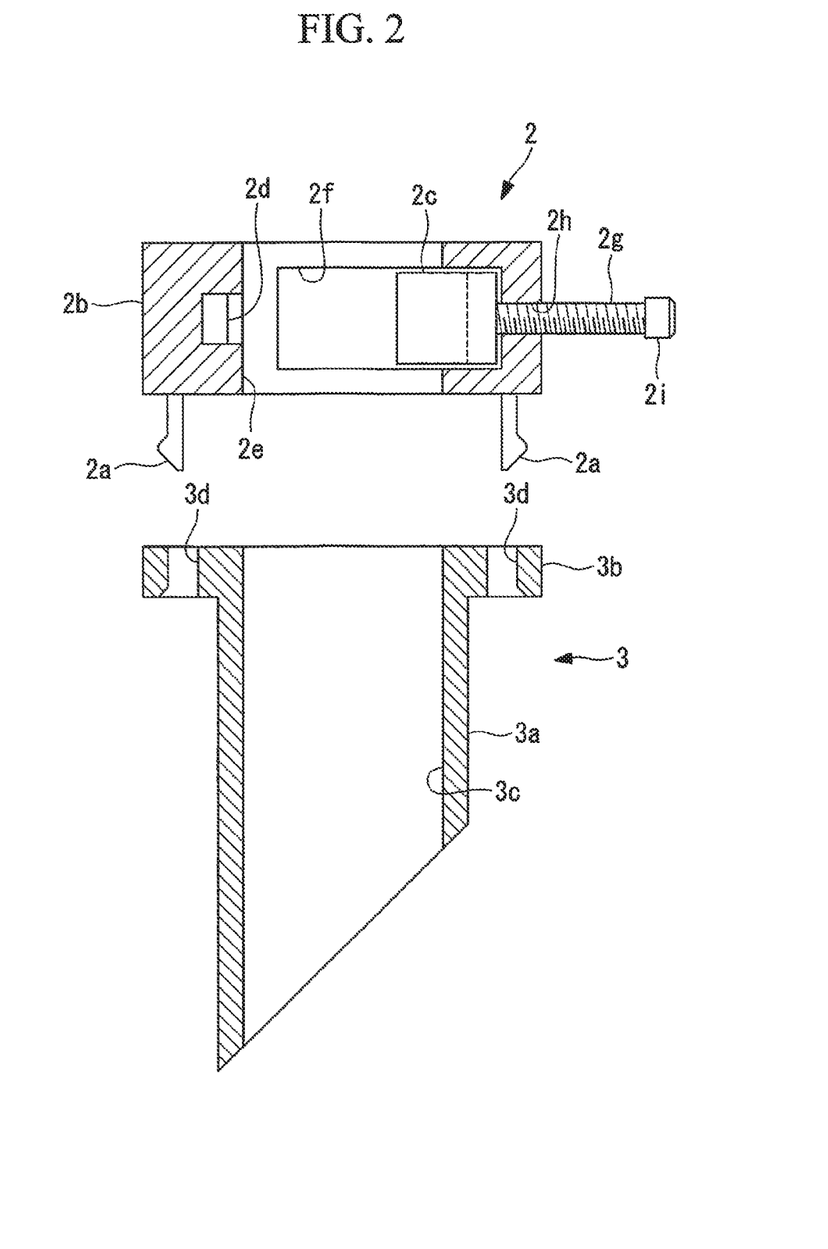
FIG. 2 is a longitudinal sectional view showing the trocar sensor unit in FIG. 1, with a trocar detached therefrom.

As shown in FIG. 2, the trocar 3 includes a tubular body 3a for insertion through the skin A and a flange 3b disposed at one end of the body 3a. The body 3a has a through-hole 3c extending in the longitudinal direction. The inner diameter of the through-hole 3c is sufficiently larger than the outer diameter of the insertion section 4 so that the insertion section 4 can be readily inserted. The flange 3b has mounting holes 3d for mounting of the trocar sensor unit 2.

As shown in FIG. 2, the trocar sensor unit 2 according to this embodiment has engagement parts 2a for engagement with the mounting holes 3d provided in the flange 3b of the trocar 3 and includes a base 2b configured to be attached to and detached from the trocar 3, a moving member 2c attached to the base 2b, and a sensor 2d attached to the base 2b.

Figure 3:
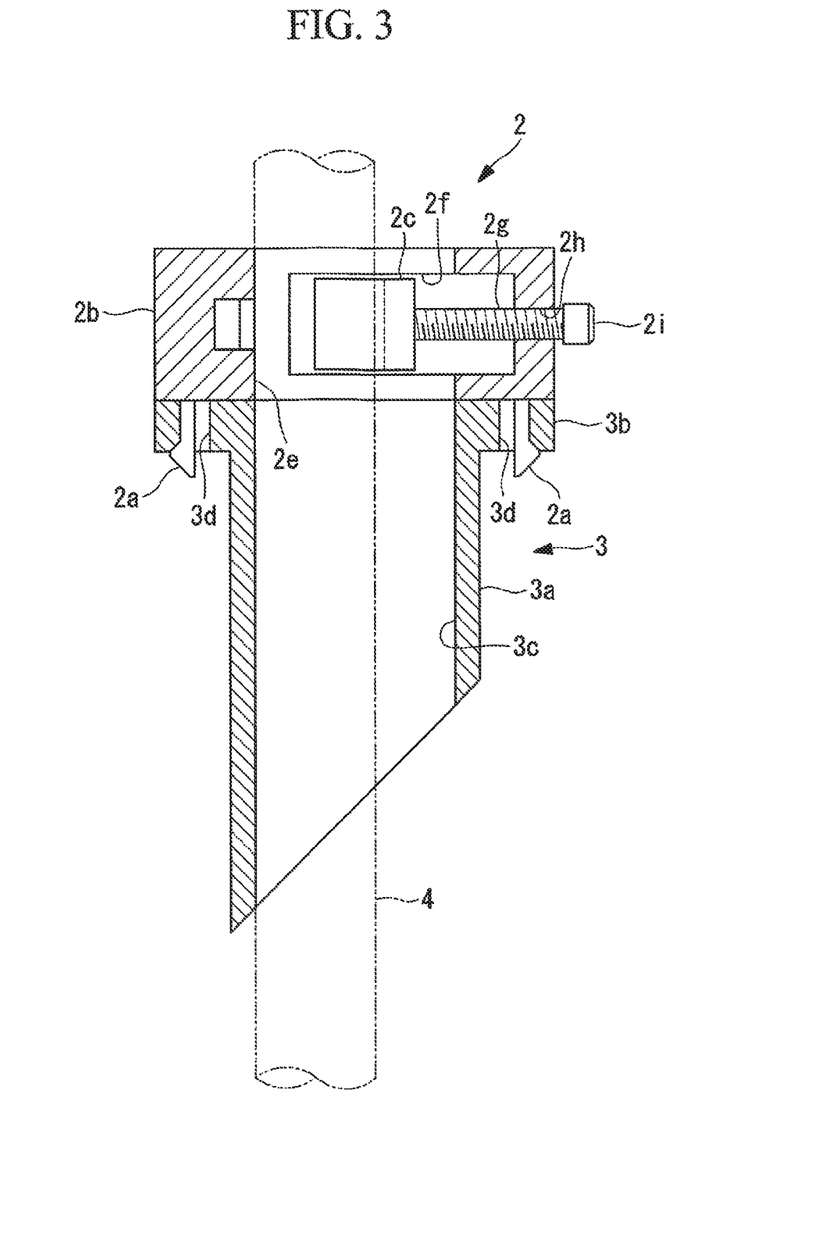
FIG. 3 is a longitudinal sectional view showing the trocar sensor unit in FIG. 1, with the trocar attached thereto.

As shown in FIG. 3, the base 2b has an inner hole 2e that has substantially the same inner diameter as the through-hole 3c of the trocar 3 and that communicates with the through-hole 3c when the base 2b is attached to the trocar 3 by bringing the engagement parts 2a into engagement with the mounting holes 3d. The inner hole 2e has a space 2f defined by a recess formed in part of the sidewall of the inner hole 2e, and the moving member 2c is disposed in the space 2f.

Figure 4:
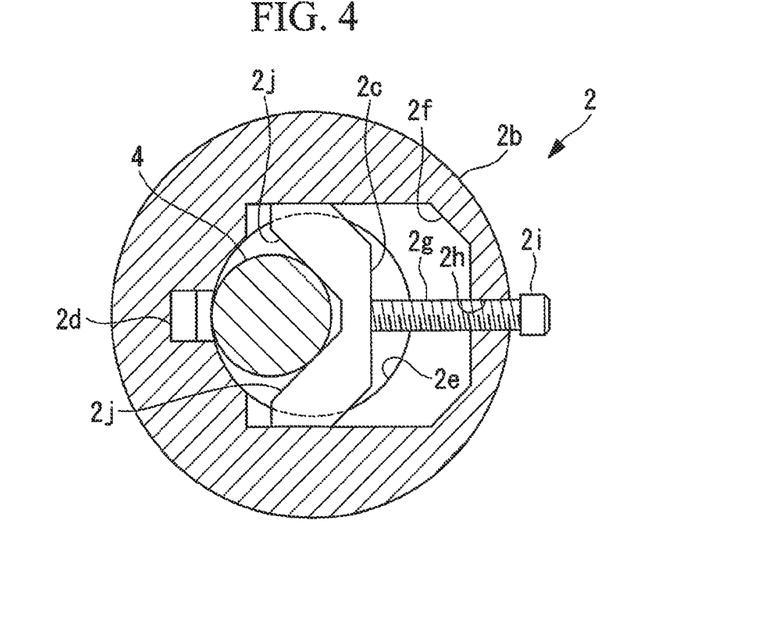
FIG. 4 is a cross-sectional view showing the trocar sensor unit in FIG. 1, with an insertion section having a small diameter inserted therein.
Figure 5:
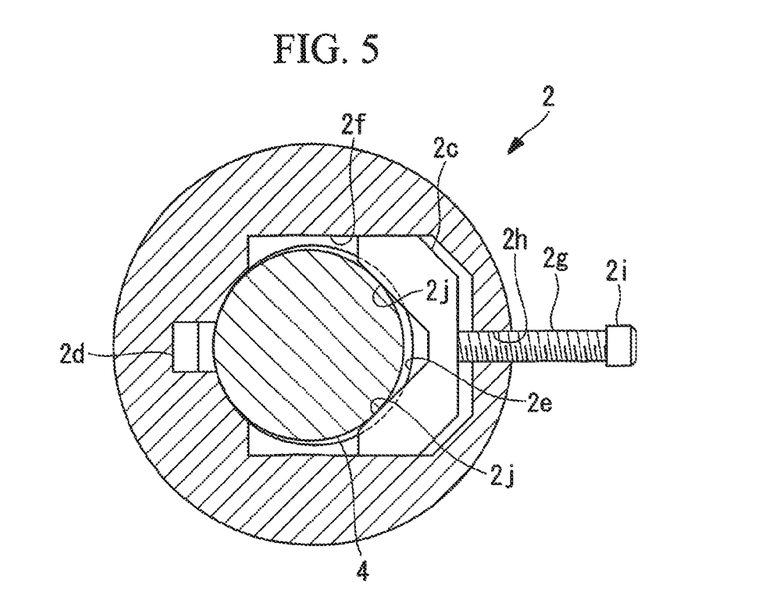
FIG. 5 is a cross-sectional view showing the trocar sensor unit in FIG. 1, with an insertion section having a large diameter inserted therein.

As shown in FIGS. 4 and 5, the moving member 2c is a V-shaped block having a V-groove formed by pressing surfaces 2j facing the inner hole 2e. The moving member 2c is disposed such that the center line of the V-groove crosses the central axis of the inner hole 2e and can be moved in the space 2f in the radial direction of the inner hole 2e. At least the pressing surfaces 2j of the moving member 2c are made of a material with a low friction coefficient, such as a silicone resin or tetrafluoroethylene resin.

A male screw 2g protruding away from the V-groove is attached to the moving member 2c so as to be rotatable about the longitudinal axis of the male screw 2g.

A female screw 2h through which the male screw 2g is threaded is formed in the base 2b. As the male screw 2g is rotated and threaded into the female screw 2h, the male screw 2g moves along the longitudinal axis of the male screw 2g, and accordingly, the moving member 2c, which is attached to the leading end of the male screw 2g, moves linearly in the space 2f.

As shown in FIG. 4, if an insertion section 4 having a small outer diameter is inserted into the inner hole 2e and the through-hole 3c, the pressing surfaces 2j of the moving member 2c are moved closer to the opposing portion of the inner wall of the inner hole 2e so that the insertion section 4 can be held, without a gap, at three positions, namely, the inner wall of the inner hole 2e and the two pressing surfaces 2j that form the V-groove.

As shown in FIG. 5, if an insertion section 4 having a large outer diameter is inserted into the inner hole 2e and the through-hole 3c, the pressing surfaces 2j of the moving member 2c are moved farther away from the opposing portion of the inner wall of the inner hole 2e so that the insertion section 4 can be inserted through the through-hole 3c. After the insertion of the insertion section 4, the pressing surfaces 2j are moved closer to the opposing portion of the inner wall of the inner hole 2e so that the insertion section 4 can be held without a gap.

The sensor 2d is an optical sensor embedded in the portion of the inner surface of the inner hole 2e opposite the pressing surfaces 2j of the moving member 2c. This optical sensor has its focus on the inner surface of the inner hole 2e and, like a laser mouse optical sensor, can measure the amounts of movement of an object moving across the inner surface of the inner hole 2e in the longitudinal axis direction and in the circumferential direction of the inner hole 2e.

The operation of the thus-configured trocar sensor unit 2 according to this embodiment will be described below.

To detect the amount of movement of the insertion section 4 inserted into the through-hole 3c of the trocar 3 with the trocar sensor unit 2 according to this embodiment, the trocar sensor unit 2 is secured to the flange 3b of the trocar 3.

When the engagement parts 2a provided on the base 2b are brought into engagement with the mounting holes 3d in the flange 3b of the trocar 3, the inner hole 2e of the base 2b is aligned with the through-hole 3c of the trocar 3. In this state, the pressing surfaces 2j of the moving member 2c are placed far away from the opposing portion of the inner surface of the inner hole 2e. As shown in FIG. 3, the insertion section 4 is inserted through the inner hole 2e and the through-hole 3c. The male screw 2g of the moving member 2c is then threaded into the female screw 2h to press the insertion section 4 with the pressing surfaces 2j in the radial direction.

Thus, the insertion section 4 is pressed between the two pressing surfaces 2j and the opposing portion of the inner surface of the inner hole 2e and is held, without a gap, at these three positions. This reduces backlash of the insertion section 4 during movement in the longitudinal axis direction and about the longitudinal axis.

Since the optical sensor 2d is embedded in the inner surface of the inner hole 2e against which the insertion section 4 is pressed, the outer surface of the insertion section 4 stays at the focal position of the optical sensor. This allows the optical sensor to accurately detect the amount of movement of the insertion section 4.

To replace the insertion section 4 with an insertion section 4 having a different diameter during surgery, the insertion section 4 to be inserted is inserted, with the moving member 2c retracted, and is held again between the two pressing surfaces 2j of the moving member 2c and the inner surface of the inner hole 2e. This allows the movement of the insertion section 4 with reduced backlash.

Thus, the trocar sensor unit 2 according to this embodiment has the advantage of allowing the amount of movement of the insertion section 4 to be accurately detected despite changes in the outer diameter of the insertion section 4 to be inserted into the through-hole 3c of the trocar 3.

Figure 6:
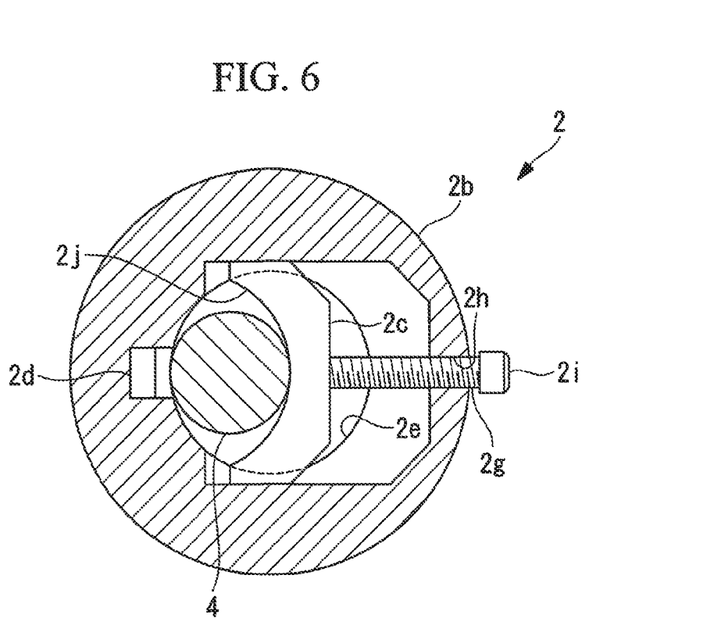
FIG. 6 is a cross-sectional view showing a first modification of the trocar sensor unit in FIG. 1.

Although the moving member 2c illustrated in this embodiment is a V-shaped block having a V-groove, the moving member 2c may have any shape that allows the object, such as the insertion section 4, inserted in the inner hole 2e to be pressed in the radial direction. For example, as shown in FIG. 6, a moving member 2c having an arc-shaped pressing surface 2j may be used, or a flat moving member 2c may be used.

Figure 7:
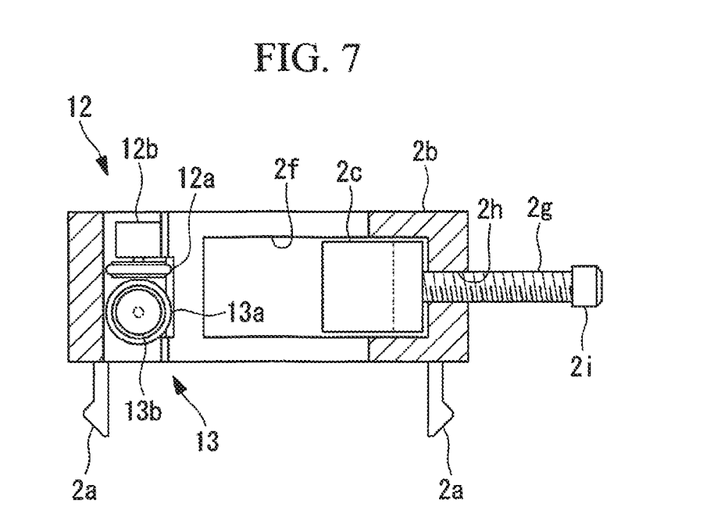
FIG. 7 is a longitudinal sectional view showing a second modification of the trocar sensor unit in FIG. 1.

The sensor 2d used in this embodiment, which detects the amount of movement of the surface of the insertion section 4, is an optical sensor that detects both the amounts of movement of the insertion section 4 in the longitudinal axis direction and in the circumferential direction; as shown in FIG. 7, it may be replaced with sensors 12 and 13 including rollers 12a and 13a disposed at positions where they contact the surface of the insertion section 4 pressed against the inner surface of the inner hole 2e by the moving member 2c and encoders 12b and 13b that detect the angles of rotation of the rollers 12a and 13a.

The rollers 12a and 13a are a first roller 12a supported so as to be rotatable about an axis parallel to the longitudinal axis of the inner hole 2e and a second roller 13a supported so as to be rotatable about an axis parallel to a tangent to the inner hole 2e. The first roller 12a rotates as the insertion section 4 rotates about the longitudinal axis, whereas the second roller 13a rotates as the insertion section 4 moves in the longitudinal axis direction.

Thus, the sensor 12 including the first roller 12a can detect the amount of movement of the insertion section 4 about the longitudinal axis, whereas the sensor 13 including the second roller 13a can detect the amount of movement of the insertion section 4 in the longitudinal axis direction.

In this embodiment, the moving member 2c is moved by threading the male screw 2g to press the insertion section 4 against the inner surface of the inner hole 2e with the pressing surfaces 2j of the moving member 2c. If the moving member 2c exerts an excessive pressing force, it is difficult to move the insertion section 4 since excessive friction occurs between the inner hole 2e and pressing surfaces 2j and the insertion section 4. If the moving member 2c exerts an insufficient pressing force, it is difficult to accurately measure the amount of movement of the insertion section 4 since a gap is formed between the inner hole 2e and moving member 2c and the insertion section 4 and thus results in backlash of the insertion section 4.

Figure 8:
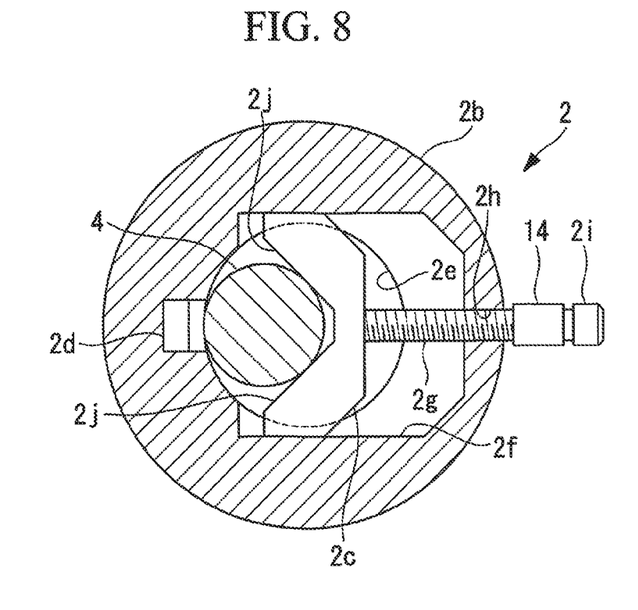
FIG. 8 is a cross-sectional view showing a third modification of the trocar sensor unit in FIG. 1.

Accordingly, as shown in FIG. 8, a clutch mechanism 14 configured to turn freely when a predetermined or higher torque is exerted thereon may be provided between a bolt head 2*i* and the male screw 2*g* to allow the moving member 2*c* to press the insertion section 4 with a suitable pressing force. In this case, the clutch mechanism 14 turns freely when a torque is applied to the bolt head 2*i* to thread the male screw 2*g* into the female screw 2*h* until the pressing force of the moving member 2*c* on the insertion section 4 reaches a predetermined level, thereby limiting the pressing force.

Figure 9:
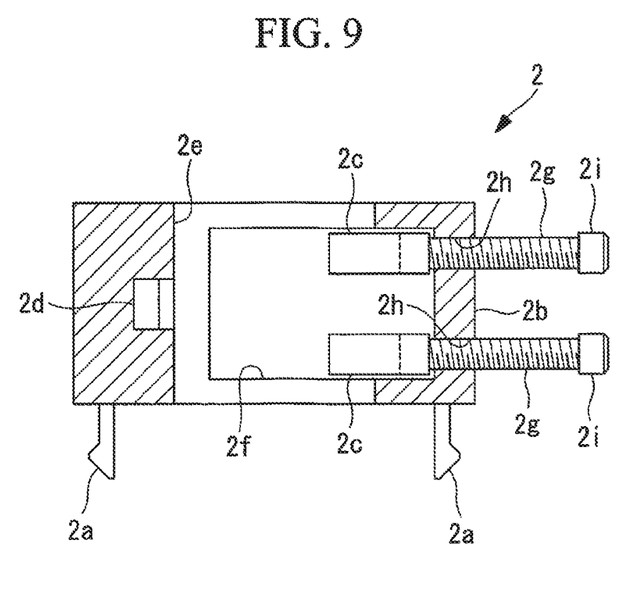
FIG. 9 is a longitudinal sectional view showing a fourth modification of the trocar sensor unit in FIG. 1.

In this embodiment, the insertion section 4 is pressed by the single moving member 2*c*; instead, as shown in FIG. 9, the insertion section 4 may be pressed by a plurality of (e.g., two) moving members 2*c* separated from each other in the longitudinal axis direction of the inner hole 2*e*. Preferably, the sensor 2*d* is disposed at a position between the moving members 2*c*. In this case, the plurality of moving members 2*c* prevent the insertion section 4 from being tilted in the inner hole 2*e* and thus allow for more accurate detection of the amount of movement of the insertion section 4.

Figure 10:
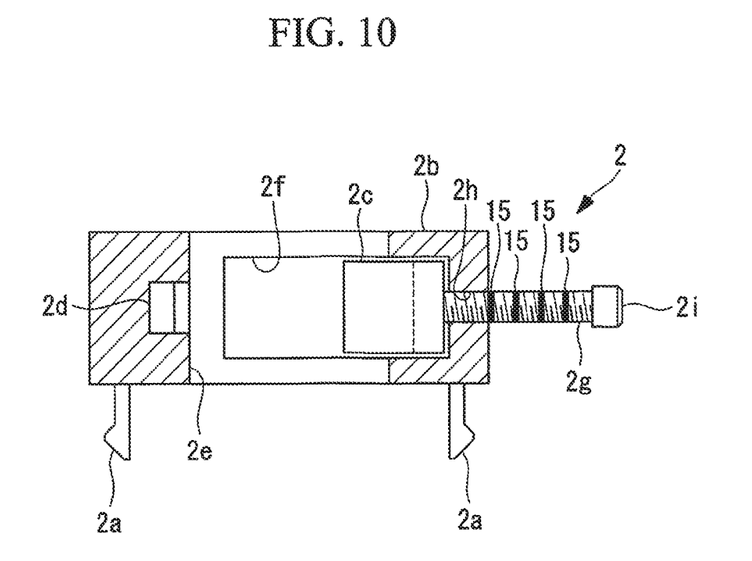
FIG. 10 is a longitudinal sectional view showing a fifth modification of the trocar sensor unit in FIG. 1.

As shown in FIG. 10, the male screw 2*g* may have markers 15 that indicate the amount of movement of the moving member. The markers 15, which are provided on the portion of the male screw 2*g* protruding from the base 2*b*, allow the position of the moving member 2*c* in the space 2*f* to be determined and can thus be used for the replacement of the insertion section 4 to check whether the insertion section 4 to be inserted next can be inserted into the gap formed between the moving member 2*c* and the inner surface of the inner hole 2*e*. For example, the markers 15 are graduation marks that can be counted to determine the position of the moving member 2*c*.

As shown in FIG. 11, a distance sensor 16 that detects the distance to the moving member 2*c* may be disposed beside the male screw 2*g*, and a calculating unit 17 that calculates the position of the moving member 2*c* from the distance detected by the distance sensor 16 and then calculates the diameter of the insertion section 4 held between the moving member 2*c* and the inner surface of the inner hole 2*e* may be provided.

Figure 12:
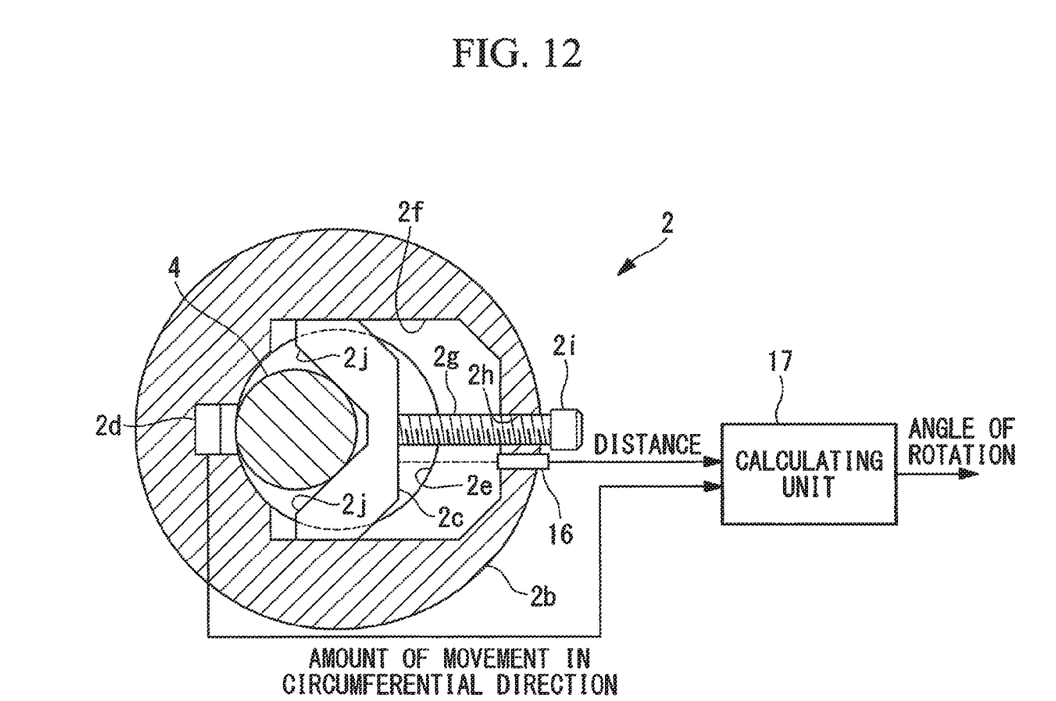
FIG. 12 is a cross-sectional view showing a seventh modification of the trocar sensor unit in FIG. 1.

As shown in FIG. 12, the calculating unit 17 may calculate the angle of rotation of the insertion section 4 from the distance detected by the distance sensor 16 and the amount of movement of the insertion section 4 in the circumferential direction, detected by the sensor 2*d*.

The calculating unit 17 may be provided in the trocar sensor unit 2 or the control unit 9.

Although the trocar sensor unit 2 according to this embodiment is configured to be attached to and detached from the trocar 3, the trocar sensor unit 2 may instead be built into the trocar 3.

The insertion section 4 to be inserted into the trocar may be either rigid or flexible.

As a result, the above-described embodiment leads to the following aspects.

One aspect of the present invention is a trocar sensor unit including a base that is configured to be attached to and detached from a trocar and that has a through-hole through which an insertion section to be inserted into the trocar is inserted; a moving member that has a pressing surface forming at least a portion of an inner surface of the through-hole of the base and that is configured to be moved in a radial direction of the through-hole; and a sensor that is disposed in at least one of the moving member and a portion of the inner surface of the through-hole opposite the pressing surface and that detects the amount of movement of a surface of the insertion section in the through-hole.

According to this aspect, the base is attached to a trocar fixed to an opening in the skin, and an insertion section of an instrument such as an endoscope is inserted into the through-hole of the base and is then inserted through the trocar into the body. In this state, the moving member is moved relative to the base in the radial direction of the through-hole to press the outer surface of the insertion section inserted in the through-hole against the inner surface of the through-hole in the radial direction with the pressing surface forming at least a portion of the inner surface of the through-hole.

Thus, the insertion section is placed in position in the radial direction irrespective of the diameter of the insertion section. Accordingly, the sensor disposed in the moving member or the portion of the inner surface of the through-hole opposite the pressing surface is placed in position relative to the outer surface of the insertion section. This allows the sensor to accurately detect the amount of movement of the surface of the insertion section irrespective of the diameter of the insertion section.

In the above aspect, the trocar sensor unit may further include a position-adjusting mechanism that adjusts the position of the moving member relative to the base.

According to this aspect, the position of the moving member relative to the base can be adjusted by actuating the position-adjusting mechanism to place the moving member at a position where the moving member prevents backlash of the insertion section in the through-hole. This improves the accuracy of the sensor to detect the amount of movement of the surface of the insertion section.

In the above aspect, the position-adjusting mechanism may include a movement-limiting mechanism that limits further movement of the moving member if a force required to move the moving member reaches or exceeds a predetermined threshold.

According to this aspect, when the position-adjusting mechanism is operated to move the moving member, the movement-limiting mechanism limits further movement of the moving member if the force required to move the moving member reaches or exceeds the predetermined threshold; therefore, the moving member can be easily placed at the position where the pressing surface contacts the surface of the insertion section with a suitable pressing force. This allows for smooth movement of the insertion section placed in position in the through-hole by the pressing surface.

In the above aspects, the moving member may have a plurality of pressing surfaces separated from each other in a longitudinal axis direction of the through-hole.

According to this aspect, the plurality of pressing surfaces arranged in the longitudinal axis direction prevent the insertion section from being tilted in the through-hole and thus allow for smooth movement of the insertion section in the through-hole.

In the above aspect, the sensor may be disposed between the plurality of pressing surfaces.

According to this aspect, the sensor can be reliably placed on the surface of the insertion section while the insertion section is prevented from being tilted, which improves the detection accuracy.

In the above aspects, the trocar sensor unit may further include an indicator that indicates the amount of movement of the moving member.

According to this aspect, the position of the pressing surface of the moving member can be determined from the amount of movement indicated by the indicator. This prevents problems such as the insertion of an insertion section having a large outer diameter into an insufficient gap between the pressing surface and the inner surface of the through-hole.

In the above aspects, the sensor may include a rotation sensor that detects the amount of movement of the surface of the insertion section in the through-hole in a circumferential direction, and the trocar sensor unit may further include a detecting unit that detects the amount of movement of the moving member.

According to this aspect, the angle of rotation of the insertion section can be calculated from the amount of movement of the surface of the insertion section in the circumferential direction, detected by the rotation sensor, and the amount of movement of the moving member detected by the detecting unit. Specifically, the angle of rotation is the amount of movement in the circumferential direction divided by the radius of the insertion section, which can be calculated from the amount of movement of the moving member detected by the detecting unit. Thus, the angle of rotation of the insertion section about the longitudinal axis in the through-hole of the trocar can be accurately calculated.

In the above aspect, the trocar sensor unit may further include a calculating unit that calculates the angle of rotation of the insertion section about a longitudinal axis from the amount of movement of the moving member detected by the detecting unit and the amount of movement in the circumferential direction detected by the rotation sensor.

According to this aspect, the calculating unit can divide the amount of movement of the insertion section in the circumferential direction by the radius of the insertion section to output the angle of rotation of the insertion section about the longitudinal axis.

Another aspect of the present invention is a trocar including a base that has a through-hole through which an insertion section is inserted and that is inserted through and fixed in an opening in a skin; a moving member that has a pressing surface forming at least a portion of an inner surface of the through-hole of the base and that is configured to be moved in a radial direction of the through-hole; and a sensor that is disposed in at least one of the moving member and a portion of the inner surface of the through-hole opposite the pressing surface and that detects the amount of movement of a surface of the insertion section in the through-hole.

In the above aspect, the trocar may further include a position-adjusting mechanism that adjusts the position of the moving member relative to the base.

In the above aspect, the position-adjusting mechanism may include a movement-limiting mechanism that limits further movement of the moving member if a force required to move the moving member reaches or exceeds a predetermined threshold.

In the above aspects, the moving member may have a plurality of pressing surfaces separated from each other in a longitudinal axis direction of the through-hole.

In the above aspect, the sensor may be disposed between the plurality of pressing surfaces.

In the above aspects, the trocar may further include an indicator that indicates the amount of movement of the moving member.

In the above aspects, the sensor may include a rotation sensor that detects the amount of movement of the surface of the insertion section in the through-hole in a circumferential direction, and the trocar may further include a detecting unit that detects the amount of movement of the moving member.

In the above aspect, the trocar may further include a calculating unit that calculates the angle of rotation of the insertion section about a longitudinal axis from the amount of movement of the moving member detected by the detecting unit and the amount of movement in the circumferential direction detected by the rotation sensor.

The present invention has the advantage of allowing the depth of insertion or another quantity to be accurately detected despite changes in the outer diameter of the insertion section to be inserted through the trocar.

REFERENCE SIGNS LIST 2 trocar sensor unit
2*b* base
2*c* moving member
2*d* sensor
2*e* inner hole (through-hole)
2*g* male screw (position-adjusting mechanism)
2*j* pressing surface
3 trocar
4 insertion section
12 sensor (rotation sensor)
14 clutch mechanism (movement-limiting mechanism)
15 marker (indicator)
16 distance sensor (detecting unit)
17 calculating unit

The invention claimed is:
1. A trocar sensor unit comprising:
 a base configured to be attached to and detached from a trocar, the base having an inner hole having a same inner diameter as a through-hole through which an insertion section to be inserted into the trocar is inserted, the base further having a space extending from the inner hole;
 a moving member having a pressing surface configured to press against the insertion section, the moving member moving in the space in a radial direction of the inner hole towards an inner surface of the inner hole; and
 a sensor disposed at at least one of the moving member and a portion of the inner surface of the inner hole opposite the pressing surface, the sensor being configured to detect an amount of movement of a surface of the insertion section in the inner hole;
 wherein the moving member includes a screw connecting to the moving member for moving the moving member in the radial direction, and
 the sensor detects a moving amount of the insertion section in the radial direction of the inner hole by moving the moving member in the radial direction of the inner hole by rotation of the screw.

2. The trocar sensor unit according to claim 1, further comprising a position-adjusting mechanism that adjusts the position of the moving member relative to the base.

3. The trocar sensor unit according to claim 2, wherein the position-adjusting mechanism comprises a movement-limiting mechanism that limits further movement of the moving member if a force required to move the moving member reaches or exceeds a predetermined threshold.

4. The trocar sensor unit according to claim 1, wherein the moving member has a plurality of pressing surfaces separated from each other in a longitudinal axis direction of the through-hole.

5. The trocar sensor unit according to claim 4, wherein the sensor is disposed between the plurality of pressing surfaces.

6. The trocar sensor unit according to claim 1, further comprising an indicator that indicates the amount of movement of the moving member.

7. The trocar sensor unit according to claim 1, wherein the sensor comprises a rotation sensor that detects the amount of movement of the surface of the insertion section in the inner hole in a circumferential direction,
the trocar sensor unit further comprising a detecting unit that detects the amount of movement of the moving member.

8. The trocar sensor unit according to claim 7, further comprising a controller comprising hardware, the controller being configured to calculate an angle of rotation of the insertion section about a longitudinal axis from the amount of movement of the moving member detected by the detecting unit and the amount of movement in the circumferential direction detected by the rotation sensor.

9. The sensor unit according to claim 1, further comprising a position-adjusting mechanism that adjusts the position of the moving member relative to the base,
wherein the position-adjusting mechanism includes a clutch mechanism configured to turn freely when a predetermined torque is exerted on the screw.

10. A trocar comprising:
a base having an inner hole having a same inner diameter as a through-hole through which an insertion section is inserted, the base further having a space extending from the inner hole, the base being configured to be inserted through and fixed in an opening in a skin;
a moving member having a pressing surface configured to press against the insertion section, the moving member moving in the space in a radial direction of the inner hole towards an inner surface of the inner hole; and
a sensor disposed at at least one of the moving member and a portion of the inner surface of the inner hole opposite the pressing surface, the sensor being configured to detect an amount of movement of a surface of the insertion section in the inner hole;
wherein the moving member includes a screw connecting to the moving member for moving the moving member in the radial direction, and
the sensor detects a moving amount of the insertion section in the radial direction of the inner hole by moving the moving member in the radial direction of the inner hole by rotation of the screw.

11. The trocar according to claim 10, further comprising a position-adjusting mechanism that adjusts the position of the moving member relative to the base.

12. The trocar according to claim 11, wherein the position-adjusting mechanism comprises a movement-limiting mechanism that limits further movement of the moving member if a force required to move the moving member reaches or exceeds a predetermined threshold.

13. The trocar according to claim 10, wherein the moving member has a plurality of pressing surfaces separated from each other in a longitudinal axis direction of the through-hole.

14. The trocar according to claim 13, wherein the sensor is disposed between the plurality of pressing surfaces.

15. The trocar according to claim 10, further comprising an indicator that indicates the amount of movement of the moving member.

16. The trocar according to claim 10, wherein the sensor comprises a rotation sensor that detects the amount of movement of the surface of the insertion section in the inner hole in a circumferential direction,
the trocar further comprising a detecting unit that detects the amount of movement of the moving member.

17. The trocar according to claim 16, further comprising a controller comprising hardware, the controller being configured to calculate an angle of rotation of the insertion section about a longitudinal axis from the amount of movement of the moving member detected by the detecting unit and the amount of movement in the circumferential direction detected by the rotation sensor.

18. A trocar sensor unit comprising:
a base configured to be attached to and detached from a trocar, the base having an inner hole having a same inner diameter as a through-hole through which an insertion section to be inserted into the trocar is inserted, the base further having a space extending from the inner hole;
a moving member having a pressing surface configured to press against the insertion section, the moving member moving in the space in a radial direction of the inner hole towards an inner surface of the inner hole; and
a sensor disposed at at least one of the moving member and a portion of the inner surface of the inner hole opposite the pressing surface, the sensor being configured to detect an amount of movement of a surface of the insertion section in the inner hole;
wherein the sensor is provided at a portion of the inner surface of the inner hole at a position opposing the pressing surface of the moving member.

* * * * *